United States Patent [19]
Hahn et al.

[11] Patent Number: 5,795,160
[45] Date of Patent: Aug. 18, 1998

[54] TAPERED DENTAL IMPLANT IN A STEPPED ORIFICE

[76] Inventors: Jack A. Hahn, 910 Barry La.. Cincinnati, Ohio 45229; Steven J. Fix, 1000 Via Viento La., Corona, Calif. 91720

[21] Appl. No.: 795,875

[22] Filed: Feb. 6, 1997

[51] Int. Cl.$^6$ .................................................. A61C 8/00
[52] U.S. Cl. .................................................. 433/174
[58] Field of Search ............................... 433/174, 173, 433/172, 175, 176

[56] References Cited

U.S. PATENT DOCUMENTS

| | | | |
|---|---|---|---|
| 3,672,058 | 6/1972 | Nikoghossian | 433/174 |
| 4,185,383 | 1/1980 | Heimke et al. | 433/173 |
| 5,199,873 | 4/1993 | Schulte et al. | 433/174 |
| 5,259,398 | 11/1993 | Vrespa | 128/898 |
| 5,527,183 | 6/1996 | O'Brien | 433/174 |

*Primary Examiner*—John J. Wilson

[57] ABSTRACT

A tapered dental implant and a method of installing the same in a stepped orifice are disclosed.

4 Claims, 2 Drawing Sheets

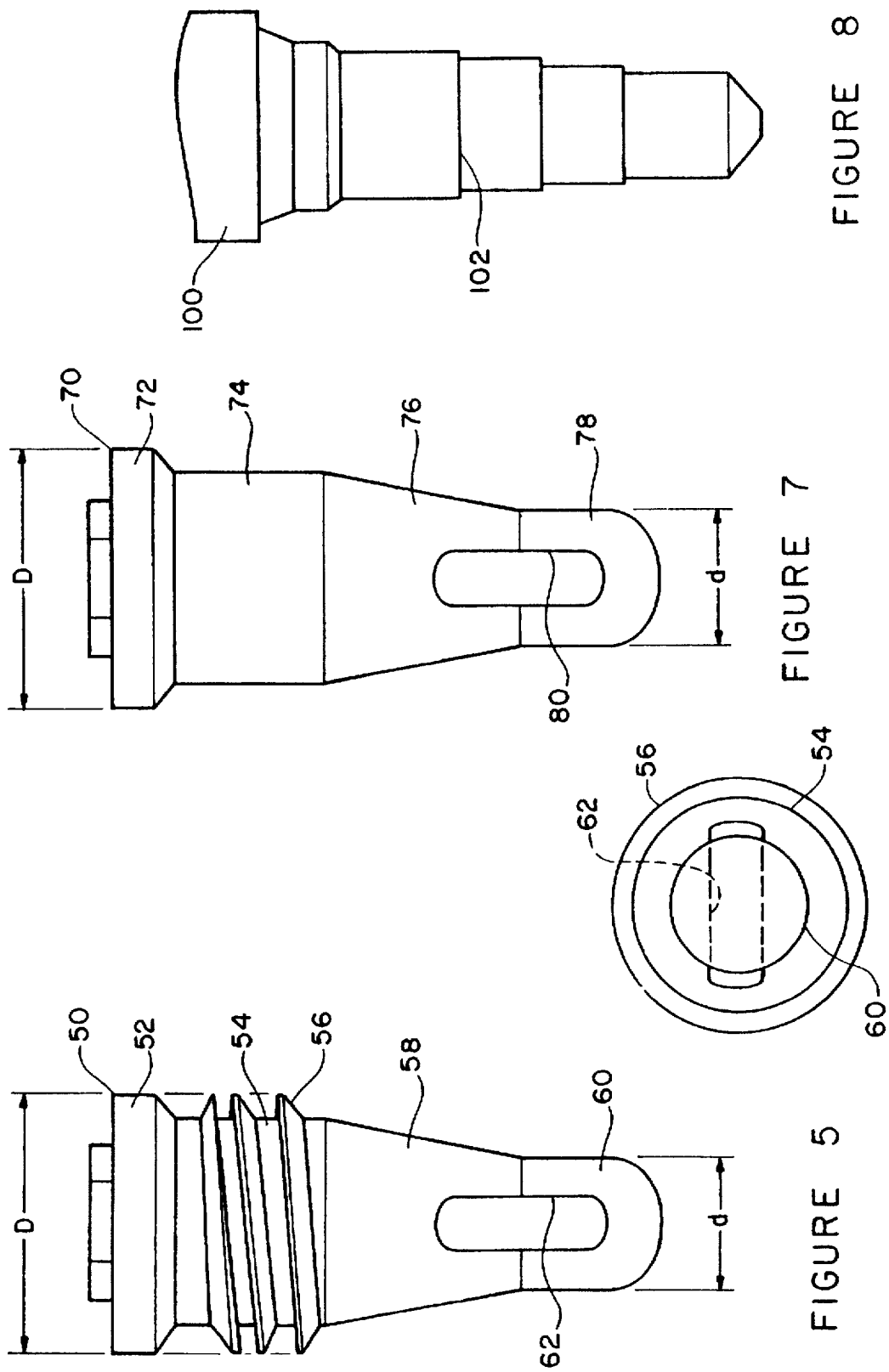

TAPERED DENTAL IMPLANT IN A STEPPED ORIFICE

FIELD OF THE INVENTION

This invention relates to dental prosthetics and, specifically, to a particular dental implant and method of installing a dental implant.

BACKGROUND OF THE INVENTION

Dental implant technology is a very well-developed technology and, over the past two decades, has become a crowded art. Important advances are being made. However, most advances are the result of careful study of problems in the field and efforts to overcome the problems by refining devices, systems and methods, rather than by revolutionary new approaches.

Tapered implants adapted to be fitted into the alveolar process of the maxilla or the mandible are very well-known and many examples of this type of dental implant are known. In cross-section, the boney structure into which the implant is to be fitted may narrow away from the alveolar crest or the bone may be of such a configuration that a straight cylindrical implant cannot readily be fitted into the bone at an angle suitable for supporting a dental prosthesis.

It is desirable to attach a dental implant firmly to both the compact tissue and the cancellous bone tissue. The compact tissue can be expanded only very slightly and it is possible to form very strong fastener joints to it; however, the cancellous bone tissue is not sufficiently dense to provide, initially, a strong fastener joint. Generally, dentists and oral surgeons rely upon the strength of the joint between a dental implant and the compact bone tissue for initial strength. In time, as the cancellous tissue in-grows around the implant and/or attaches to the implant, the implant becomes more firmly secured in the bone.

It would, of course, be desirable to obtain a greater initial strength securement between the implant and the bone, and efforts in this direction have been made. For example, U.S. Pat. No. 2,857,670, to Kiernan, Jr., discloses a rather complex tapered implant which includes lateral pins that, after insertion into an orifice in the bone, are forced outwardly into the cancellous tissue. Such an implant would, of course, be virtually impossible to remove without severe damage to the bone.

Another approach is to coat the implant with a substance that promotes attachment or to modify the surface of the implant to accelerate in-growth and/or attachment. A tapered implant embodying various forms of this concept is described in U.S. Pat. No. 4,051,598 to Sneer.

Dental implants having an etched surface to promote tissue attachment and in-growth are described in U.S. Pat. No. 4,826,434 to Krueger and in U.S. Pat. No. 4,826,434 to Mozsary, et.

U.S. Pat. No. 4,722,870 to White, et. al., discloses a metal-ceramic composite material for the manufacture of prosthetic devices by casting a suitable metal, such a Vitallium™, into a hydroxyapatite and/or whitlockite investment with three-dimensional interconnected porosity. The resulting composite is finished to provide a surface for attachment to bone.

Hydroxyapatite has long been used as a coating for dental implants to increase the strength of the bond between the boney tissue and the implant, and combinations o f hydroxyapatite and whitlockite are well-known as tissue growth promoting coatings, see, e.g. Aoki, et. al., U.S. Pat. No. 4,149,893.

In all instances, however, little, if any, immediate strength is gained from using tissue growth enhancement coated dental implants.

As pointed out above, many tapered dental implants are known. The following patent disclosures are mentioned as exemplary of teachings of devices of this type: U.S. Pat. No. 2,609,604; U.S. Pat. No. 2,857,670; U.S. Pat. No. 4,051,598; U.S. Pat. No. 4,244,689; U.S. Pat. No. 4,290,756; U.S. Pat. No. 4,411,624; U.S. Pat. No. 4,468,200; U.S. Pat. No. 4,713,003; U.S. Pat. No. 4,758,160; U.S. Pat. No. 4,870,080; U.S. Pat. No. 5,000,686 and U.S. Pat. No. 5,470,230.

Of the known prior art, only two devices provide a direct approach to the need for forming a stronger immediate attachment of the dental implant to the cancellous tissue of the maxilla or mandible. U.S. Pat. No. 2,857,670, to Kiernan, Jr., has been mentioned. U.S. Pat. No. 5,470,230 to Daftary, et. al., uses a "molly bolt" type of arrangement for expanding the distal end of a dental implant outwardly against the bone after the implant is installed in the orifice. While such an approach recognizes the need for a solution, the solution is a rather complex mechanical arrangement and applies considerable pressure on the bottom of the orifice into which the implant is inserted.

This invention is directed specifically to the need for providing greater initial strength to a dental implant installation.

It is known to provide a stepped orifice in the maxilla or mandible for implant installation. For example, U.S. Pat. No. 5,199,873 to Schulte, et. al., discloses a stepped implant for installation in a stepped orifice for the expressed purpose of making it possible to install the implant more quickly than is possible with other implants. No immediate strength advantage is mentioned or achieved, however. The Schulte, et. al., implant, or one very similar to it, is believed to be marketed in Europe under the trademark FRIALIT®.

SUMMARY OF THE INVENTION

A method of installing a dental implant is disclosed. A stepped endosseous orifice is drilled into the bone into which the implant is to be installed. A specifically shaped and dimensioned tapered implant is inserted into the orifice. The tapered implant is constructed and configured to define a proximal end, a cylindrical portion distally adjacent to the proximal end, and a frustoconically tapered portion tapering from a major diameter D of the cylindrical portion to a minor diameter d proximate the distal end of the implant. The orifice is step drilled such that the orifice is alternatingly of equal or lesser diameter than the respective portions of the implant to be installed adjacent such steps. This arrangement results in laterally compressing the cancellous tissue in portions of the orifice to form a tight fitting sleeve of bone around the implant without exerting undue lateral force bone into which implant is installed. A preferred tapered implant additionally comprises a helical thread extending from the cylindrical portion and from the frustoconically tapered portion, the helical thread diminishing in depth toward the distal end of the implant.

The invention is also embodied in a dental implant constructed and configured to define a proximal end, a cylindrical portion distally adjacent to the proximal end, a frustoconically tapered portion tapering from a major diameter D of the cylindrical portion to a minor diameter d proximate the distal end of the implant, a helical thread extending from the cylindrical portion and from the frustoconically tapered portion, the helical thread diminishing in thread depth from the frustoconically tapered portion toward the distal end of the implant.

BRIEF DESCRIPTION OF THE DRAWINGS

FIGS. 5 and 6, respectively, depict a side elevational view and a bottom view of an alternative dental implant for use in this invention.

FIG. 7 is a side elevational view of yet another embodiment of a dental implant for use in this invention.

FIG. 8 is a side elevational view showing the relative diameters of portions of a stepped osteotome that can be used to form a stepped orifice as shown in FIG. 4.

DESCRIPTION OF THE PREFERRED EMBODIMENTS

The drawings depict exemplary forms of dental implants that are suitable for use in this invention and the methods described herein are exemplary of such uses. Variations in both the implant and the method are within the scope of the invention.

Figure 1:
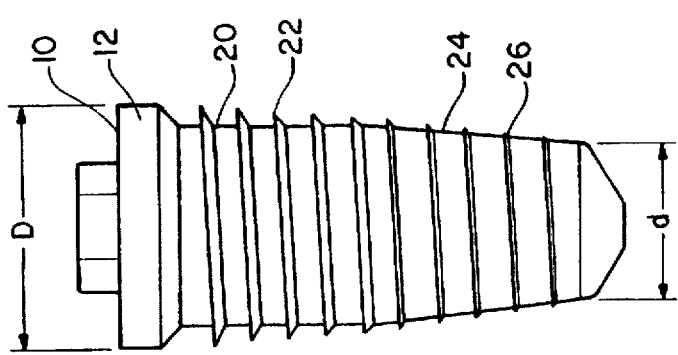
FIG. 1 is a side elevational view depicting a preferred form of the tapered implant screw of this invention.

A example of the preferred embodiment of the dental implant of this invention is shown in an elevational, partial cross-sectional, view in FIG. 1 to which reference is first made. This implant is preferably manufactured in titanium but other materials may be used.

Figure 3:
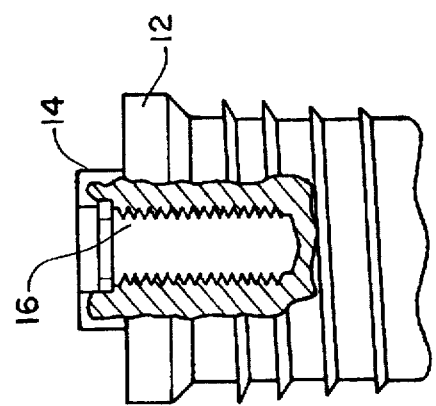
FIG. 3 is a partial view of the upper portion, as drawn, of the tapered implant screw depicted in FIG. 1, partially cut away in cross-section showing the inner structure of the threaded orifice therein.
Figure 2:
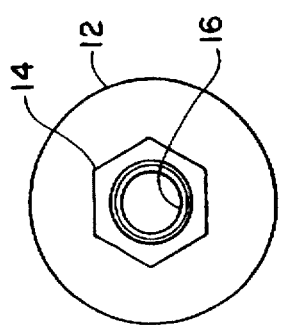
FIG. 2 is a top plan view of the tapered implant screw of FIG. 1 showing the top structure, including a threaded orifice.

Referring to the exemplary implant 10 in FIGS. 1, 2 and 3, the proximal end 12, shown at the top in FIG. 1, is circular overall with a raised hexagonal driving nut 14 extending from the circular portion approximately 1 mm to permit the implant to be turned by a suitable wrench. A threaded orifice 16 extends from the proximal end coaxially with the round implant for receiving a screw for attaching a prosthesis to the implant. The screw and the prosthesis are not, per se, part of this invention and any of a great many prosthetic devices may be used. Optionally, the proximal end to the orifice 16 may be configured to provide a hexagonal driving portion.

Extending distally from the top, downwardly as shown in FIG. 1, the implant is configured and constructed to define a cylindrical portion 20 having a helical thread portion 22 extending therefrom. The thread portion 22 is preferably generally of the type described by Krueger in U.S. Pat. No. 4,826,434, or a modification thereof wherein the thread has a flat surface facing away from the distal end of the implant and a tapered end facing toward the distal end of the implant. In the example of FIG. 1, the outer periphery of the thread 22 is truncated to define a cylindrical helix. The type of thread is not, however, the essence of the invention and the thread 22 is exemplary only.

Distally of the cylindrical portion 20, the implant is constructed and configured to define a generally frustoconically tapered portion 24 having a tapered thread portion 26 continuing the helical thread begun at 22. The implant has a major diameter D, which in the embodiment of FIG. 1 is the diameter of the top and the upper threads, and a minor diameter, proximate the distal end of the implant, d, as indicated in FIG. 1. The tapered thread portion 26 has a thread depth at its proximal extremity, where the cylindrical thread portion 22 begins, substantially the same as the depth of the threads 22 and tapering to a thread depth approaching zero at the distal end of the implant. The extreme distal end of the implant is rounded or forms a very oblique frustocone to permit easy entrance into an endosseous orifice.

Figure 4:
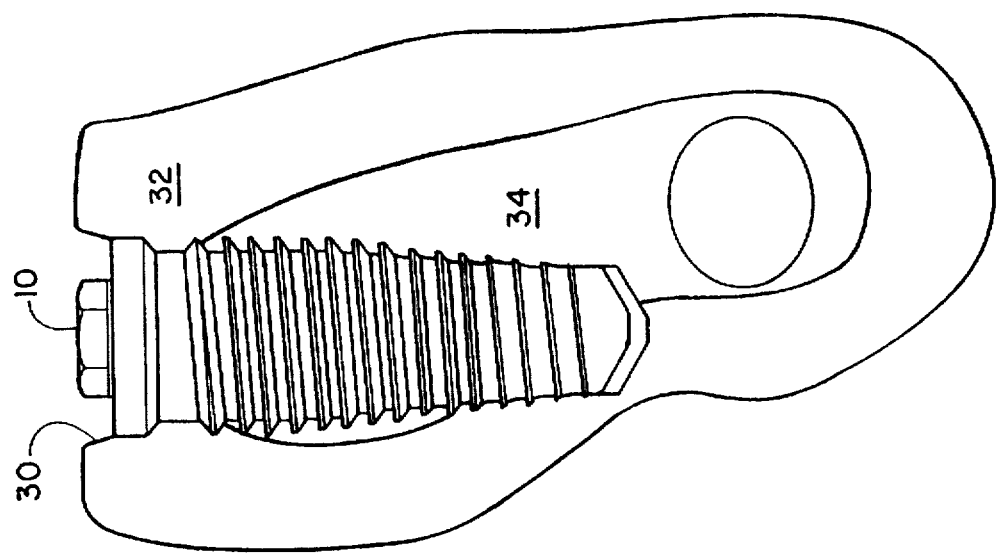
FIG. 4 depicts the configuration of the tapered implant screw overlaying the stepped orifice, showing the general diametrical relationship of the tapered implant screw relative to the stepped orifice.

Referring now to FIG. 4, according to the method of this invention, a stepped orifice is formed in the maxilla or mandible. From the top of the compact layer of the bone, a stepped endosseous orifice 30 is formed, which, preferably is formed to define a tapered portion part way through the compact layer as indicated by line 32. The orifice is so formed as to define a plurality of steps, one of which is indicted at 34 in FIG. 4. The number of steps, two or more, is not critical. Four or five steps have been found generally to be optimal.

The outer configuration of the implant 10 is outlined in heavy lines indicated. In use, the implant 10 is, according to the present method, screwed into a stepped endosseous orifice 30 of critical diameter and step relationship shown in FIG. 4. The stepped orifice may be formed in the using a plurality of increasing diameter drills or a stepped drill, or a plurality of increasing diameter osteotomes or a stepped osteotome. FIG. 8 depicts the outer diametrical outline of a drill or an osteotome 100 showing the stepped relationship, details of cutting edges, etc., being omitted for clarity of illustration, which is suitable for use in forming a stepped orifice as described. The osteotome 100 defines a plurality of steps, one of which is indicated at 102 that correspond to the desired number, diameter and depth of the steps to be formed in the bone. As mentioned, a plurality of osteotomes or a stepped osteotome may be used to form the stepped orifice and may be advantageous in that the cancellous tissue may be pre-compacted using the microtome and/or other orifice-forming tools before the implant is installed.

The diameters of the steps are so configured and dimensioned that the diameter of the orifice in the maxilla or mandible is generally less than the diameter of that portion of the implant that will be screwed, or pressed or otherwise fitted, into the orifice in the maxilla or mandible. The diameter of the orifice may, in certain areas, be equal to the diameter of the implant portion to be positioned therein, but the average diameter of the orifice is always less than the average diameter of the implant. This is a very important relationship.

As the implant is inserted into the orifice by screwing it in, as described, the cancellous tissue is laterally compressed and may be longitudinally displaced in some places to form a tight fitting sleeve of bone around the implant, very importantly, without exerting undue force on the maxilla or mandible cross-section. The structure and relationship described causes local compression and displacement of the cancellous tissue which is transmitted principally along the walls of the orifice rather than entirely laterally to the peripheral portion of the bone.

The implant 10 of FIG. 1 may, of course, be manufactured in any desired diameter and length. Typically implants are manufactured in diameters from about 4 to 6 mm and a length of from 8 or 20 mm so as to provide a size that is suitable for use in a variety of maxilla or mandible sizes and configurations.

The implant, when used in the method described, provides many advantages. The implant and orifice are anatomically proper and can be used in nearly all circumstances. The thread is graduated from near zero in the narrow portion of the bone to avoid applying high lateral pressure on the bone to quite deep, from about 0.5 mm on the smaller implants to about 1.1 mm on larger diameter implants, in the proximal cylindrical portion where the cancellous tissue is deeper.

The implant surface is not, per se, a pale of the present invention. It is desirable, however, to take advantage of surface technologies that enhance tissue in-growth and adhesion to the implant. Etched or other specially prepared surfaces are desirably used, as well as surface coatings such as hydroxyapatite.

The implant and method are useful in tapered bone areas and, properly used, avoids buccal-lingual perforations at the apical portion. The design allows optimum placement position for better load distribution and maximum estethics. The specially designed thread configuration allow placement in all types of bone and, due to thread shape, the implant can be self-threading. Shapes and diameters allow for maximum surface to bone contact in anatomically compromised bone. The tapered apex helps prevent anterior maxillary wall perforation as well as avoiding injury to adjacent teeth adjacent at the apex. The wide top provides better load distribution preventing shear forces so as to maintain crestal bone. The thread being more aggressive at the top helps maintain crestal bone height. The configuration of implant allows simple insertion of a cylindrical type with the stability of a screw securement.

The taper of the implant allows for more flexibility in angulation of the osteotomy where there are anatomical limitations in the area of the apex of the osteotomy. The doctor will be able to place a longer implant without having to sacrifice angulation and/or the maximum coronal surface area for the implant to abutment interface. The diminishing thread on the taper allows the thread to be formed in the osteotomy by laterally compressing the bone increasing the bone density rather than cutting away the bone, this is a desirable feature for cases with lower quality of bone and where preservation of the quantity of bone is desired. The taper also provides a more anatomical shape (shaped like a tooth) which fits better in a tooth extraction site, for an immediate extraction implant placement procedure.

Alternative implant 50, shown in FIGS. 5 and 6, is similar as to the major and minor diameters but the distal portion is not threaded. The head portion 52 is of the configuration described with reference to implant 10 and the cylindrical portion 54 and helical thread portion 56 are generally similar to the corresponding proximal portions in implant 10. The intermediate portion 58 having the major diameter D tapers to a distal cylindrical portion 60 having a minor diameter d. The implant is so configured as to define a passage 62 through the intermediate and distal portions to permit in-growth of the cancellous tissue and the surface is specially treated and/or coated to promote tissue attachment.

Alternative implant 70, shown in FIG. 7, is also similar as to the major and minor diameters to the corresponding features of implant 10, but neither the proximal cylindrical portion nor the distal portion is threaded. The head portion 72 is of the configuration described with reference to implant 10 and the cylindrical portion 74 generally similar to the corresponding proximal portions in implant 10, except for the absence of threads. The intermediate portion 76 having the major diameter D tapers to a distal cylindrical portion 78 having a minor diameter d. The implant is so configured as to define a passage 80 through the intermediate and distal portions to permit in-growth of the cancellous tissue and the surface is specially treated and/or coated to promote tissue attachment.

Each of these alternative embodiments is used in generally the same way as described with reference to implant 10, except that in the case of implant 70, the implant is inserted without screwing it into position. Turning the implant during insertion may, nevertheless, be advantageous in obtaining a firm seating in the stepped orifice.

It will be understood that variations are within the scope of the art. For example, any proximal driving configuration may be used and many types of threads may be used without departing from the invention as defined in the appended claims.

INDUSTRIAL APPLICATIONS

This invention is useful in the dental implant industry, in dentistry and oral surgery.

What is claimed is:

1. A method of installing a dental implant comprising the steps of:

drilling a stepped endosseous orifice in the maxilla or mandible of the patient in which the implant is to be installed; and inserting into said orifice a tapered implant, the tapered implant being so constructed and configured as to define a proximal end, a cylindrical portion adjacent to the proximal end, a frustoconically tapered portion tapering from the major diameter D at the proximal end of the implant to a minor diameter d proximate the distal end of the implant; said orifice being step drilled such that the orifice less than or equal to respective portions of the implant to be installed adjacent such steps for laterally compressing the cancellous tissue to form a tight fitting sleeve of bone around the implant without exerting undue lateral force bone into which implant is installed.

2. The method of claim 1 wherein insertion of the tapered implant comprises screwing the insert into the orifice and wherein the implant additionally comprises a helical thread extending from the cylindrical portion and from the frustoconically tapered portion.

3. The method of claim 2 wherein the helical thread diminishes in depth toward the distal end of the implant.

4. A dental implant constructed and configured to define a proximal end, a cylindrical portion adjacent to the proximal end having a major diameter D, a frustoconically tapered portion tapering to a minor diameter d proximate the distal end of the implant, a single helical thread extending from the cylindrical portion and from the frustoconically tapered portion, said single helical thread diminishing in thread depth from the frustoconically tapered portion toward the distal end of the implant.

* * * * *